United States Patent
Ismail et al.

(10) Patent No.: US 12,144,355 B1
(45) Date of Patent: Nov. 19, 2024

(54) **METHOD FOR INHIBITING FUNGAL GROWTH USING *PYROPIA YEZOENSIS***

(71) Applicant: KING FAISAL UNIVERSITY, Al-Ahsa (SA)

(72) Inventors: Ahmed Mahmoud Ismail, Al-Ahsa (SA); Eman Said Eshewy, Giza (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/544,256

(22) Filed: Dec. 18, 2023

(51) Int. Cl.
*A01N 65/03* (2009.01)
*A01P 3/00* (2006.01)
*C12N 1/12* (2006.01)

(52) U.S. Cl.
CPC ............... *A01N 65/03* (2013.01); *A01P 3/00* (2021.08); *C12N 1/12* (2013.01)

(58) Field of Classification Search
CPC .............. A01N 65/03; A01P 3/00; C12N 1/12
See application file for complete search history.

(56) References Cited

U.S. PATENT DOCUMENTS

| 8,758,769 B2 | 6/2014 | Nam et al. |
| 2021/0298326 A1 | 9/2021 | Zotter et al. |

FOREIGN PATENT DOCUMENTS

| CA | 3211734 A1 * | 9/2022 | ............. A01N 65/03 |
| KR | 20170042390 A | 4/2017 | |
| WO | 1998010656 A1 | 3/1998 | |

OTHER PUBLICATIONS

Perez M J, et al. "Antimicrobial Action of Compounds from Marine Seaweed", Marine Drugs, Mar. 9, 2016,14(3):52, 38 pages; doi: 10.3390/md14030052. (Year: 2016).*

Berthon J-V , et al.,"Seaweed and Microalgae as Major Actors of Blue Biotechnology to Achieve Plant Stimulation and Pest and Pathogen Biocontrol", J. Agricultural Sci, Dec. 9, 2021,pp. 532-534; DOI: https://doi.org/10.1017/S0021859621000885. (Year: 2021).*
Lee JY et al "Anti-inflammatory Effects of Pyropia yezoensi</i>s Extract in LPS-stimulated RAW 264.7 cells" Korean Journal of Fisheries and Aquatic Sciences (KJFAS), Dec. 31, 2014, 47(6),757-764 (incl. machine tranlaiton, 7pp.); doi: 10.5657/KFAS.2014.0757. (Year: 2014).*
Park J-S, et al "Physiological activities and bioactive compound from laver (Pyropia yezoensis) hydrolysates by using subcritical water hydrolysis" The Journal of Supercritical Fluids, Jun. 2019 (ePub Mar. 3, 2019), 148, pp. 130-136; doi:10.1016/j.supflu.2019.03.004. (Year: 2019).*
Machine translation of CA 3211734 A1 (Nguema-Ona, Emmanuel Eric), 116 pp. (Year: 2022).*
De Corato, et al. "Antifungal activity of crude extracts from brown and red seaweeds by a supercritical carbon dioxide technique against fruit postharvest fungal diseases" ScienceDirect, vol. 131, Sep. 2017, pp. 16-30 https://doi.org/10.1016/j.postharvbio.2017.04.011.
Hughes, et al."Antibacterial Activity of Seaweed Extracts against Plant Pathogenic Bacteria" Journal of Bacteriology and Mycology, pp. 2-11, Jul. 10, 2019, ISSN : 2471-0172.
Berthon, et al.,"Seaweed and microalgae as major actors of bluebiotechnology to achieve plant stimulation and pest and pathogen biocontrol", Published online by Cambridge University Press: Dec. 9, 2021, DOI: https://doi.org/10.1017/S0021859621000885.
Jimenez, et al. "Anti-Phytopathogenic Activities of Macro-Algae Extracts" Marine Drugs 2011, 9(5), 739-756, https://doi.org/10.3390/md9050739.
Perez, et al. "Antimicrobial Action of Compounds from Marine Seaweed", Marine Drugs, 2016, Mar. 14(3): 52.DOI: 10.3390/md14030052.

* cited by examiner

*Primary Examiner* — Aaron J Kosar
(74) *Attorney, Agent, or Firm* — Nath, Goldberg & Meyer; Joshua B. Goldberg

(57) ABSTRACT

A method of preventing or inhibiting fungal infestation of plants using an extract of *Pyropia yezoensis*. In an embodiment, the fungal infestation is caused by *Podosphera xanthii*. In an embodiment, the plants comprise a cucurbit plant. In an embodiment, the cucurbit plant comprises cucumber.

8 Claims, 1 Drawing Sheet

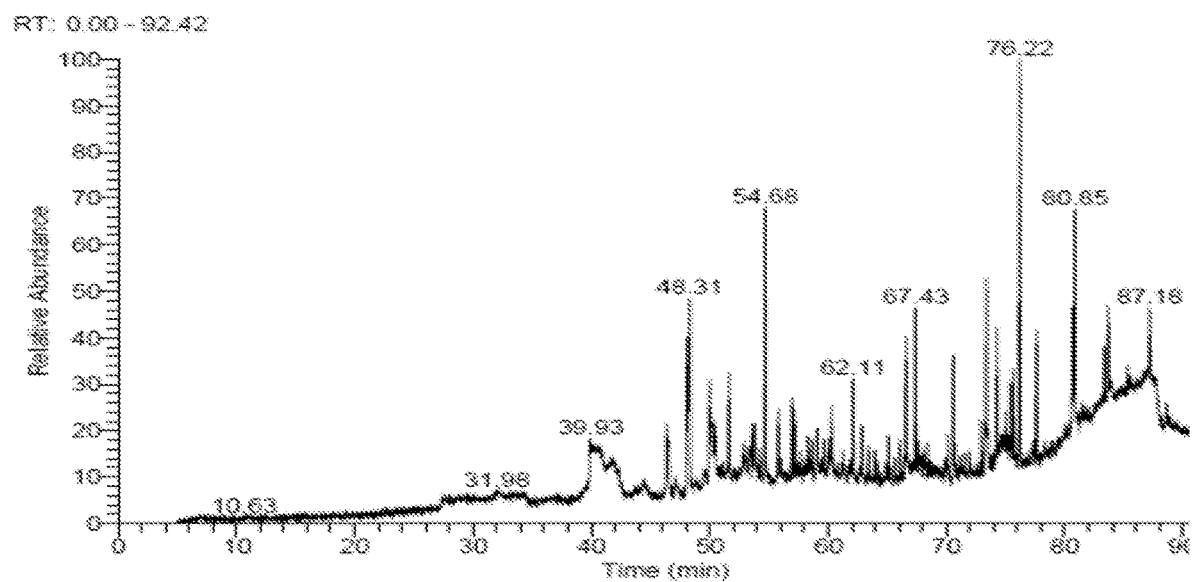

METHOD FOR INHIBITING FUNGAL GROWTH USING *PYROPIA YEZOENSIS*

BACKGROUND

1. Field

The present disclosure relates to inhibiting fungal growth and, particularly, to a method of inhibiting fungal growth using *Pyropia yezoensis*.

2. Description of the Related Art

The red algae *Pyropia* or *Porphyra* holds the distinction of being the most extensively consumed seaweed globally. Its use as a food source in East Asia dates to ancient times. The species, *Pyropia yezoensis*, for example, is the main farm seaweed in Korea.

There is a continuing need to find new compositions having superior biological properties for use in controlling or preventing infestation of plants by phytopathogenic fungi, such as *Podosphera xanthii*, which is the causal agent of powdery mildew disease of cucurbit plants. For example, compositions which are sustainable and have reduced environmental impact are needed for effective control of phytopathogens.

Thus, a method for inhibiting fungal growth solving the aforementioned problems is desired.

SUMMARY

In an embodiment, the present subject matter relates to a method of preventing or inhibiting fungal infestation of plants using an extract of *Pyropia yezoensis*. In an embodiment, the fungal infestation is caused by *Podosphera xanthii*. In an embodiment, the plants comprise a cucurbit plant. In an embodiment, the cucurbit plant comprises cucumber.

According to an embodiment, the present subject matter relates to a pesticidal composition, comprising an extract of *Pyropia yezoensis* and an agriculturally acceptable carrier. In one embodiment, a method of preventing or inhibiting fungal infestation of plants comprises providing the pesticidal composition and contacting the pesticidal composition with the plants.

These and other features of the present subject matter will become readily apparent upon further review of the following specification.

BRIEF DESCRIPTION OF THE DRAWINGS

The sole FIGURE presented herein shows GC/MS analysis of the ethanol extract of *P. yezoensis*.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a method of preventing or inhibiting a fungal infestation of plants using an extract of *Pyropia yezoensis*. In an embodiment, the extract is an alcohol extract. In an embodiment, the alcohol extract is an ethanol extract. In an embodiment, the fungal infestation is caused by *Podosphera xanthii*. In an embodiment, the plants comprise a cucurbit plant. In an embodiment, the cucurbit plant comprises cucumber.

In an embodiment, the method includes applying the extract of *Pyropia yezoensis* to the plants, e.g., by spraying the soil and/or aerial parts of the plant. In an embodiment, the soil of the plant comprises the soil from which the plant grows. In an embodiment, the application can be carried out using, for example, water as a carrier by customary spraying techniques using spray liquor amounts of from about 100 to 1000 l/ha (for example from 300 to 400 l/ha).

In other embodiments, the present subject matter relates to a pesticidal composition, comprising an extract of *Pyropia yezoensis* and an agriculturally acceptable carrier. Non-limiting examples of suitable carriers include water, mineral earths such as, for example, silica gels, silicates, talc, kaolin, attaclay, limestone, lime, chalk, bole, loess, clay, dolomite, diatomaceous earth, calcium sulfate, magnesium sulfate, magnesium oxide, and ground synthetic materials; fertilizers, such as, for example, ammonium sulfate, ammonium phosphate, ammonium nitrate, and ureas; products of vegetable origin, such as, for example, cereal meal, tree bark meal, wood meal and nutshell meal; cellulose powders; polyvinylpyrrolidone; and other solid carriers.

In one embodiment, a method of preventing or inhibiting fungal infestation of plants comprises providing the pesticidal composition and contacting the pesticidal composition with the plants.

An embodiment of the present subject matter is directed to a method of making a pesticidal composition including mixing the *Pyropia yezoensis* extract with an agriculturally acceptable carrier. For example, the method of making a pesticidal composition can include mixing the *Pyropia yezoensis* extract under sterile conditions with an agriculturally acceptable carrier with preservatives, buffers, and/or propellants to create the pesticidal composition.

In experiments, HPLC analysis of an ethanol extract of *Pyropia yezoensis* led to the identification and quantification of 19 phenolic compounds in the ethanolic extract of *P. yezoensis* (Table 1).

TABLE 1

Phenolic compounds detected and quantified in *P. yezoensis* extract

| | *P. yezoensis* | | |
|---|---|---|---|
| Phenolic compounds | Area | Area | Conc · µg/g DW |
| Gallic acid | 43.65 | 201.78 | 904.73 |
| Chlorogenic acid | 19.46 | 80.92 | 559.33 |
| Catechin | 2.30 | 1.76 | 20.68 |
| Methyl gallate | 8.17 | 3.59 | 9.48 |
| Coffeic acid | 2.14 | 0.00 | 0.00 |
| Syringic acid | 0.00 | 1.51 | 6.05 |
| Pyro catechol | 0.00 | 0.00 | 0.00 |
| Rutin | 0.86 | 0.00 | 0.00 |
| Ellagic acid | 0.00 | 0.00 | 0.00 |
| Coumaric acid | 0.00 | 0.00 | 0.00 |
| Vanillin | 2.27 | 0.00 | 0.00 |
| Ferulic acid | 0.00 | 0.00 | 0.00 |
| Naringenin | 0.99 | 1.19 | 5.81 |
| Rosmarinic acid | 1.61 | 0.88 | 4.92 |
| Daidzein | 6.00 | 0.00 | 0.00 |
| Querectin | 1.22 | 0.00 | 0.00 |
| Cinnamic acid | 8.44 | 0.00 | 0.00 |
| Kaempferol | 0.00 | 0.00 | 0.00 |
| Hesperetin | 6.29 | 5.34 | 12.14 |
| Total | | | 1523.13 |

The GC/MS analysis (see the sole FIGURE) of the ethanol extract of *P. yezoensis* led to the detection of 50 compounds, which constituted 100% of the total compounds (Table 2). Cholest-3,5-diene, Methyl stearate, methyl 14-methylpentadecanoate, cholest-5-en-3-ol, erucylamide, 1H-Purin-6-amine, [(2-fluorophenyl)methyl] and 2,3-dihydroxypropyl palmitate were detected in the *P. yezoensis* extract with high values donating 43.2%, respectively. The ethanol extract also contained flavonoids (Luteolin 6,8-di-C-glucoside), alkaloid (Pseudojervine and N-methylasimilobine), volatile compounds (Ethyl iso-allocholate), alcohol (Ethanol, 2-[2-[2-[4-(1,1,3,3-tetramethylbutyl)phenoxy]ethoxy]ethoxy]) and other fatty acids in small ratios.

TABLE 2

Chemical composition of *P. yezoensis*, extract

| Retention time (min.) | Compound Name | Formula | Value of total compounds % | Molecular weight |
|---|---|---|---|---|
| 48.09 | Methyl 14-Methylpentadecanoate | $C_{17}H_{34}O_2$ | 7.05 | 270 |
| 48.31 | Palmitic acid, methyl ester | $C_{17}H_{34}O_2$ | 3.96 | 270 |
| 50.02 | 2,3-dihydroxypropyl palmitate | $C_{19}H_{38}O_4$ | 4.16 | 330 |
| 50.39 | Ethyl Octadecanoate | $C_{20}H_{40}O_2$ | 1.07 | 312 |
| 51.6 | 1H-Purin-6-amine, [(2-fluorophenyl)methyl]- | $C_{12}H_{10}FN_5$ | 4.39 | 243 |
| 52.9 | 3',4',7-Trimethoxyquercetin | $C_{18}H_{16}O_7$ | 1.27 | 344 |
| 53.25 | Octadec-9-enoic acid | $C_{18}H_{34}O_2$ | 0.62 | 282 |
| 53.32 | Linolenic acid, 2-hydroxy-1-(hydroxymethyl)ethyl ester (Z,Z,Z)- | $C_{21}H_{36}O_4$ | 0.99 | 352 |
| 53.8 | 10-Octadecenoic acid, methyl ester | $C_{19}H_{36}O_2$ | 3.68 | 296 |
| 54.23 | 1,1-Dimethyltetradecyl hydrosulfide | $C_{16}H_{34}S$ | 1.12 | 258 |

TABLE 2-continued

Chemical composition of *P. yezoensis* extract

| Retention time (min.) | Compound Name | Formula | Value of total compounds % | Molecular weight |
|---|---|---|---|---|
| 54.68 | Methyl stearate | $C_{19}H_{38}O_2$ | 7.38 | 298 |
| 55.78 | 18,19-Secoyohimban-19-oic acid, 16,17,20,21-tetradehydro-16-(hydroxymethyl)-, methyl ester,(15á,16E)- | $C_{21}H_{24}N_2O_3$ | 2.06 | 352 |
| 57.21 | Stearic acid, ethyl ester | $C_{20}H_{40}O_2$ | 1.72 | 312 |
| 57.65 | 2-Hexadecanol | $C_{16}H_{34}O$ | 0.72 | 242 |
| 58.63 | N-methylasimilobine N-oxide | $C_{18}H_{19}NO_3$ | 2.17 | 297 |
| 59.06 | 2-[4-methyl-6-(2,6,6-trimethylcyclohex-1-enyl)hexa-1,3,5-trienyl]cyclohex-1-en-1-carboxaldehyde | $C_{23}H_{32}O$ | 1.27 | 324 |
| 59.65 | 2-(2-[4-(1,1,3,3-Tetramethylbutyl) phenoxy]ethoxy)ethanol | $C_{18}H_{30}O_3$ | 0.97 | 294 |
| 60.05 | Phenol, 3-([2-(aminocarbothioyl)hydrazono]methyl)acetate | $C_{10}H_{11}N_3O_2S$ | 0.97 | 237 |
| 60.29 | Octadecanoic acid, 4-hydroxy-, methyl ester | $C_{19}H_{38}O_3$ | 2.03 | 314 |
| 61.25 | cis-13-Eicosenoic acid | $C_{20}H_{38}O_2$ | 0.92 | 310 |
| 62.83 | Octadecanamide | $C_{18}H_{37}NO$ | 1.19 | 283 |
| 63.36 | p-Cresol, 2,2'-methylenebis[6-tert-butyl- | $C_{23}H_{32}O_2$ | 0.86 | 340 |
| 63.95 | 6-Azacholest-4-en-7-one, 6-benzyl-3à-hydroxy- | $C_{33}H_{49}NO_2$ | 0.74 | 491 |
| 64.23 | 17-Pentatriacontene | $C_{35}H_{70}$ | 0.70 | 490 |
| 65.14 | 2-Phenyl-1,3-dioxolan-4-yl)methyl palmitate, cis | $C_{26}H_{42}O_4$ | 0.99 | 418 |
| 65.66 | Ethyl iso-allocholate | $C_{26}H_{44}O_5$ | 0.62 | 436 |
| 66.11 | Pirenzepine, 8-sulfamoyl- | $C_{19}H_{22}N_6O_4S$ | 1.06 | 430 |
| 67.42 | 1,2-Benzenedicarboxylic acid | $C_{24}H_{38}O_4$ | 3.74 | 390 |
| 67.66 | 3,6,9,12-Tetraoxatetradecan-1-ol, 14-[4-(1,1,3,3-tetramethylbutyl)phenoxy]- | $C_{24}H_{42}O_6$ | 0.85 | 426 |
| 68.1 | Ethanol, 2-[2-[2-[4-(1,1,3,3-tetramethylbutyl)phenoxy]ethoxy]ethoxy]- | $C_{20}H_{34}O_4$ | 0.79 | 338 |
| 68.18 | Stearic acid, 3-(octadecyloxy)propyl ester | $C_{39}H_{78}O_3$ | 0.57 | 594 |
| 68.45 | Corynan-17-ol, 18,19-didehydro-10-methoxy-, acetate (ester) | $C_{22}H_{28}N_2O_3$ | 0.84 | 368 |
| 70.16 | 4H-Cyclopropa[5',6']benz[1',2':7,8]azuleno[5,6-b]oxiren-4-one, 8,8a-bis(acetyloxy)-2a-[(acetyloxy)methyl]-1,1a,1b,1c,2a,3,3a,6a,6b,7,8,8a-dodecahydro-6bhydroxy- 3a-methoxy-1,1,5,7-tetramethyl-, [1aR-(1aà,1bá,1cà,2aà,3aá,6aà,6bà,7á,8á,8aà)]- | $C_{27}H_{36}O_{10}$ | 0.91 | 520 |
| 71.17 | Luteolin 6,8-di-C-glucoside | $C_{27}H_{30}O_{16}$ | 0.62 | 610 |
| 71.54 | 1,25-Dihydroxyvitamin D3, TMS derivative | $C_{30}H_{52}O_3Si$ | 0.42 | 488 |
| 71.95 | Oleic acid, 3-(octadecyloxy)propyl ester | $C_{39}H_{76}O_3$ | 0.76 | 592 |
| 72.98 | Pseudojervine | $C_{33}H_{49}NO_8$ | 1.31 | 587 |
| 73.37 | Erucylamide | $C_{22}H_{43}NO$ | 4.80 | 337 |
| 73.43 | 7,8-Epoxylanostan-11-ol, 3-acetoxy- | $C_{32}H_{54}O_4$ | 1.40 | 502 |
| 75.05 | Propanoic acid, 2-(3-acetoxy-4,4,14-trimethylandrost-8-en-17-yl)- | $C_{27}H_{42}O_4$ | 1.07 | 430 |
| 75.44 | Cholest-5-en-3-yl stearate | $C_{45}H_{80}O_2$ | 1.67 | 652 |
| 75.67 | Cholesta-4,6-dien-3-ol | $C_{27}H_{44}O$ | 2.12 | 384 |
| 76.22 | Cholest-3,5-diene | $C_{27}H_{44}$ | 10.22 | 368 |
| 77.33 | Cholesteryl myristate | $C_{41}H_{72}O_2$ | 0.52 | 596 |
| 80.59 | 1-Hydroxy-2-(2,3,4,6-tetra-O-acetyl-beta-d-glucopyranosyl)-9H-xanthene-3,6,7-triyl triacetate | $C_{33}H_{34}O_{18}$ | 0.51 | 718 |
| 80.85 | Cholest-5-en-3-ol | $C_{27}H_{46}O$ | 5.20 | 386 |
| 83.34 | Cholesterol, oleate | $C_{45}H_{78}O_2$ | 1.34 | 650 |
| 85.29 | Cholest-5-en-3-ol (3α)-, acetate | $C_{29}H_{48}O_2$ | 0.71 | 428 |
| 87.18 | Cholesteryl valerate | $C_{32}H_{54}O_2$ | 2.05 | 470 |
| 91.71 | Propanoic acid, 2-(3-acetoxy-4,4,14-trimethylandrost-8-en-17-yl)- | $C_{27}H_{42}O_4$ | 2.86 | 430 |

In experiment, the extract of *P. yezoensis* exhibited great antifungal activity against *Podosphera xanthii*, the causal agent of powdery mildew disease of cucumber, and recorded a lowest Disease Severity (DS) level of 15.03% and a low Area Under the Disease Progress Curve (AUDPC) value of 280.75%. Accordingly, the extract of *P. yezoensis* has the potential to make a significant contribution as an antifungal agent that is more sustainable and ecofriendly than traditional chemical fungicides.

It is to be understood that the present methods are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method of preventing or inhibiting fungal infestation of cucumber plants, comprising:
   selecting cucumber plants infested with *Podosphera xanthii*;
   providing an extract of *Pyropia yezoensis*; and
   contacting the extract of *Pyropia yezoensis* with the cucumber plants.

2. The method of claim 1, wherein the extract is an alcohol extract of *Pyropia yezoensis*.

3. The method of claim 1, wherein the alcohol extract is an ethanol extract.

4. The method of claim 1, wherein contacting the extract of *Pyropia yezoensis* with the plants comprises contacting the extract of *Pyropia yezoensis* with at least one of soil and aerial parts of the plants.

5. A method of preventing or inhibiting fungal infestation of cucumber plants, comprising:
   selecting cucumber plants infested with *Podosphera xanthii*;
   providing a pesticidal composition comprising an extract of *Pyropia vezoensis* and an agriculturally acceptable carrier; and
   contacting the extract of *Pyropia yezoensis* with the plants.

6. The method of claim 5, wherein the extract is an alcohol extract of *Pyropia yezoensis*.

7. The method of claim 6, wherein the alcohol extract is an ethanol extract.

8. The method of claim 5, wherein contacting the pharmaceutical composition with the plants comprises contacting the pharmaceutical composition with at least one of soil and aerial parts of the plants.

* * * * *